(12) United States Patent
Stauch et al.

(10) Patent No.: US 12,324,612 B2
(45) Date of Patent: Jun. 10, 2025

(54) INTRAMEDULLARY NAIL FOR DISTRACTING A LONG BONE

(71) Applicant: ORTHOFIX S.R.L., Bussolengo (IT)

(72) Inventors: Roman Stauch, Assamstadt (DE); Martina Müller, Bad Mergentheim (DE); Sebastian Hammel, Assamstadt (DE)

(73) Assignee: Orthofix S.R.L., Bussolengo (IT)

( * ) Notice: Subject to any disclaimer, the term of this patent is extended or adjusted under 35 U.S.C. 154(b) by 320 days.

(21) Appl. No.: 17/636,076

(22) PCT Filed: Aug. 20, 2020

(86) PCT No.: PCT/EP2020/073302
§ 371 (c)(1),
(2) Date: Feb. 17, 2022

(87) PCT Pub. No.: WO2021/032823
PCT Pub. Date: Feb. 25, 2021

(65) Prior Publication Data
US 2022/0287745 A1 Sep. 15, 2022

(30) Foreign Application Priority Data
Aug. 20, 2019 (DE) .................. 10 2019 122 354.7

(51) Int. Cl.
*A61B 17/72* (2006.01)
(52) U.S. Cl.
CPC ...... *A61B 17/7216* (2013.01); *A61B 17/7233* (2013.01)

(58) Field of Classification Search
CPC ........................... A61B 17/72–7291
See application file for complete search history.

(56) References Cited

U.S. PATENT DOCUMENTS

| 5,415,660 A | * | 5/1995 | Campbell | .......... | A61B 17/7216 606/68 |
| 6,033,412 A | * | 3/2000 | Losken | .............. | A61B 17/7216 606/57 |

(Continued)

FOREIGN PATENT DOCUMENTS

| DE | 19700225 A1 | 7/1998 |
| DE | 10340025 A1 | 3/2005 |

(Continued)

OTHER PUBLICATIONS

International Searching Authority/European Patent Office, "International Search Report" for PCT/EP2020/073302, mailed Nov. 20, 2020, 5 pages.

(Continued)

*Primary Examiner* — Eduardo C Robert
*Assistant Examiner* — Steven J Cotroneo
(74) *Attorney, Agent, or Firm* — Haynes and Boone, LLP

(57) ABSTRACT

An intramedullary nail for distracting a long bone, comprising a first tube extending in an axial direction of the intramedullary nail, a second tube extending in an axial direction of the intramedullary nail, which is coupled with the first tube to be axially displaceable within one another, a first locking opening in an end area of the first tube facing away from the second tube, and a coil, which is disposed in a coil area of the first tube between the first locking opening and the second tube.

14 Claims, 3 Drawing Sheets

(56) References Cited

U.S. PATENT DOCUMENTS

| | | | |
|---|---|---|---|
| 6,416,516 B1* | 7/2002 | Stauch | A61F 2/3662 |
| | | | 606/62 |
| 7,063,706 B2 | 6/2006 | Wittenstein | |
| 7,753,915 B1* | 7/2010 | Eksler | A61B 17/7016 |
| | | | 606/86 R |
| 9,439,694 B2* | 9/2016 | Kraus | A61N 1/326 |
| 11,207,110 B2* | 12/2021 | Pool | A61B 17/1725 |
| 2004/0138663 A1 | 7/2004 | Kosashvili et al. | |
| 2005/0246034 A1* | 11/2005 | Soubeiran | A61B 17/7216 |
| | | | 623/23.45 |
| 2013/0072932 A1* | 3/2013 | Stauch | A61B 17/7241 |
| | | | 606/63 |
| 2013/0165733 A1* | 6/2013 | Rogachefsky | A61B 17/80 |
| | | | 600/12 |
| 2014/0236311 A1 | 8/2014 | Vicatos et al. | |
| 2017/0172624 A1* | 6/2017 | Brunner | A61B 17/7016 |
| 2017/0244287 A1 | 8/2017 | Haaja | |
| 2017/0333080 A1* | 11/2017 | Roschak | A61B 17/68 |
| 2018/0353214 A1* | 12/2018 | Kiester | A61B 17/7004 |
| 2019/0015138 A1* | 1/2019 | Schwardt | A61B 17/66 |

FOREIGN PATENT DOCUMENTS

| | | |
|---|---|---|
| DE | 102015109624 A1 | 12/2016 |
| EP | 1033112 B1 | 9/2000 |
| JP | 2009254804 A | 11/2009 |
| WO | 2012051512 A1 | 4/2012 |

OTHER PUBLICATIONS

International Searching Authority/United States Patent Office, "Notification of Transmittal of the International Preliminary Report on Patentability" for PCT/EP2020/073302, mailed Oct. 7, 2021, 7 pages.

Japanese Patent Office, Notice of Reasons for Refusal, Japanese Patent Application No. 2022-506445, dated Mar. 11, 2024, 6 pages (with machine translation).

* cited by examiner

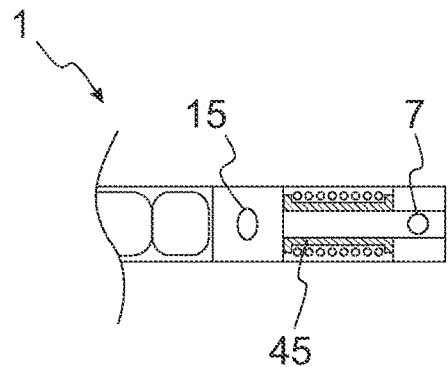
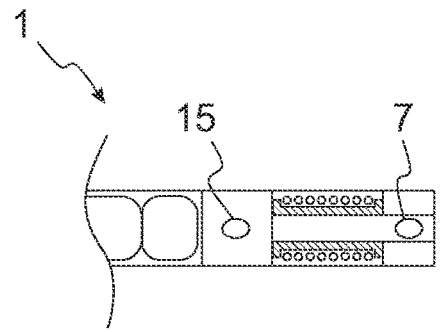
Fig. 5A                Fig. 5B
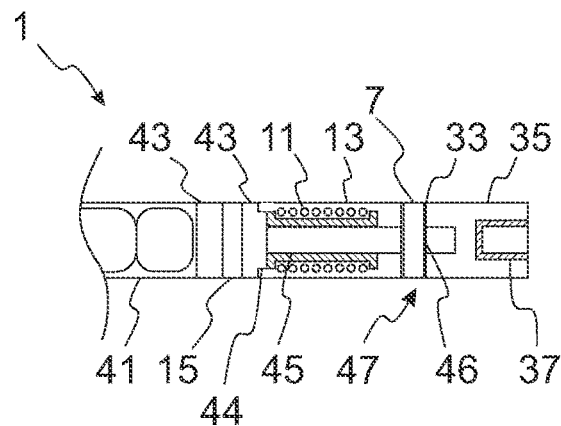
Fig. 6
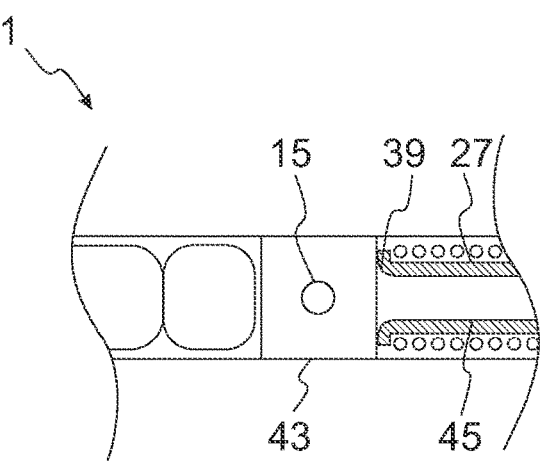
Fig. 7

INTRAMEDULLARY NAIL FOR DISTRACTING A LONG BONE

CROSS-REFERENCE TO RELATED APPLICATION(S)

The present application claims priority under 35 U.S.C. 365 to International Patent Application No. PCT/EP2020/073302, filed Aug. 20, 2020, entitled "Intramedullary Nail for Distracting a Long Bone", which claims priority to German patent Application No. 102019122354.7, filed Aug. 20, 2019, both of which are incorporated herein by reference into the present application fully set forth herein.

FIELD OF THE INVENTION

The invention relates to an intramedullary nail for distracting a long bone.

STATE OF THE ART

Intramedullary nails are known from the state of the art, which enable oblong long bones to be distracted. Two bone fragments, a first bone fragment and a second bone fragment, are displaced relative to one another by means of an intramedullary nail. At the contact point between the two bone fragments, bone is intended to grow anew. This is achieved by selecting a feed rate of a drive of the intramedullary nail for distraction to be sufficiently low. It is known to supply an intramedullary nail in the transcutaneous way with energy for the drive. From EP 1 033 112 B1, reception antennae are known, which are disposed within a housing of an intramedullary nail or at the front side outside the housing of an intramedullary nail.

Hitherto known solutions from the state of the art, however, have restrictions in terms of the energy transmission performance or the efficiency of the energy transmission, need more space or require the intramedullary nail to be coupled with a reception antenna disposed outside the intramedullary nail.

BACKGROUND

It is a task of the invention to propose an intramedullary nail, which is improved with respect to the state of the art. In particular, an intramedullary nail should enable a high energy transmission performance, should have a high efficiency of the energy transmission, should occupy little space in the bone or should be able to be implanted near the joint. Furthermore, intramedullary nails are desirable, which require the least possible surgical effort or enable a reliable fixation in the bone fragments.

According to one aspect of the invention, an intramedullary nail for distracting a long bone is provided with a first tube extending in an axial direction of the intramedullary nail, a second tube extending in an axial direction of the intramedullary nail and coupled with the first tube to be axially displaceable within one another, a first locking opening in an end area of the first tube facing away from the second tube, and a coil, which is disposed in a coil area of the first tube between the first locking opening and the second tube.

A further aspect of the invention relates to a method for transmitting energy from a primary coil to a coil of an intramedullary nail in one of the typical embodiments described herein, including energizing the primary coil and receiving, by the coil of the intramedullary nail, at least a part of the electromagnetic energy emitted by energizing the primary coil.

Exemplary intramedullary nails are in particular suitable for treating fractures or other damages of oblong long bones, wherein other damages can be, for example, bone losses due to tumors or impacts of violence. Bones, which can be treated with typical intramedullary nails, are thigh bones (femur) and shinbones (tibia), however, upper arm bones (humerus), ell bones (ulna), radius bones (radius) and splinter bones (fibula) can also be treated.

In typical embodiments, the second tube is displaceable within the first tube in an axial direction. In further typical embodiments, the first tube is displaceable within the second tube in an axial direction. Typically, the terms "axial" and "radial" herein are to be understood with respect to the longitudinal axis of the intramedullary nail, with the longitudinal axis extending in particular along the intramedullary nail or the largest spatial expansion of the intramedullary nail. In particular, an axial direction is to be understood as a direction along or in parallel to the longitudinal axis of the intramedullary nail, a radial direction is to be understood as a direction perpendicular to the longitudinal axis. The longitudinal axis of an intramedullary nail may also be curved, for example, in an intramedullary nail having a continuous bend according to Herzog for lower legs. Typically, the intramedullary nail is at least substantially circular in a cross section to the longitudinal axis of the intramedullary nail.

In typical embodiments, the coil is realized as a reception coil or as a secondary coil. The coil is typically arranged to receive energy from an extracorporeally disposed primary coil, in particular for operating a drive of the intramedullary nail. The primary coil is typically realized as a toroidal coil or as a saddle coil. Typically, the coil is assigned to the first tube. Typically, the coil is disposed in or at the first tube.

In typical embodiments, the intramedullary nail and the primary coil are set up for transcutaneous data transmission between the coil and the primary coil. Typically, the intramedullary nail comprises a data processing unit for sending data via the coil or for reading data received via the coil.

Typical embodiments have a locking opening, in particular a first locking opening in an end area of the first tube. Typically, a locking opening is arranged to insert or pass through a locking means for locking the intramedullary nail in a bone fragment of the long bone, in particular in a first bone fragment or in a second bone fragment. In this way, the intramedullary nail can be connected to the bone fragment of the long bone to be fixed in all directions and all rotational directions. The intramedullary nail can thus be connected fixedly to the bone fragment in all degrees of freedom. Bolts or screws are in particular possible as the locking means. The screws or bolts enable the intramedullary nail to be anchored within the bone fragment.

In typical embodiments, a locking opening is oriented at a fixed angle. A fixed-angle orientation may offer the advantage of being able to tension two or more locking openings or locking means with respect to one other. Typically, a locking opening runs through the intramedullary nail in a radial direction. In further typical embodiments, a locking opening encloses an angle with the longitudinal axis of the intramedullary nail, with the angle being in particular less than 110° or less than 100°. In typical embodiments, the angle is greater than 70°, for example, greater than 80°. Typically, two or more locking openings are oriented in parallel relative to one another. In further typical embodiments, two or more locking openings are oriented to be twisted relative to one another. In particular, the locking openings are twisted relative to one another by at most 7°, by way of example at most 5°. Typically, the locking openings are oriented to be intersecting or skewed relative to one another.

In typical embodiments, the first tube is produced of at least two interconnected tube pieces. The tube pieces typically are interconnected, welded together, bonded together or connected by form closure using a joining process. Typically, the tube pieces comprise an end piece in the end area of the first tube, a mandrel in the coil area, a hollow piece at the end of the first tube opposite the end area, or an intermediate piece in an intermediate area between the mandrel and the hollow piece. Herein, the tube pieces are in particular not to be understood as being restricted to the mentioned areas of the first tube, but in typical embodiments also extend into other areas of the first tube. The mandrel may, for example, extend into the end area and may in particular include a locking opening. Moreover, two or more of the tube pieces, for example, the mandrel and the intermediate piece, may be produced in one piece.

Typically, the first tube, in particular the second tube as well, are composed substantially of metal or a metal alloy, in particular of biocompatible metal or a biocompatible metal alloy.

In typical embodiments, at least one hollow piece of the first tube is substantially composed of metal or a metal alloy, in particular of biocompatible metal or a biocompatible metal alloy. In embodiments, the hollow piece, the intermediate piece, the end piece or the mandrel of the first tube is composed substantially of metal or a metal alloy, in particular of biocompatible metal or a biocompatible metal alloy. In typical embodiments, an end piece, a mandrel or an intermediate piece is at least substantially composed of plastics, for example, of epoxy resin, silicone, or thermoplastic resin. Typically, a tube piece of metal is coupled to a further tube piece of plastics by form closure.

In exemplary embodiments, the mandrel is welded or bonded to the end piece, overmolded with it or otherwise coupled to it.

In typical embodiments, the first tube has a smaller outer diameter in the coil area. "To have a smaller outer diameter" may mean, for example, that a constriction in sections or a tapering in sections is present. In the coil area, the coil is typically arranged radially outside on the first tube. Typically, the coil encompasses the first tube. Typically, the coil is realized to be axially symmetrical.

Herein, an outer diameter of an intramedullary nail, of a tube piece or a coil envelope is to be understood as the outer diameter of the intramedullary nail, the tube piece or the coil envelope in a cross section to the longitudinal axis of the intramedullary nail.

In typical embodiments, the coil is a cylindrical coil and arranged coaxially with the intramedullary nail. In further typical embodiments, the coil is realized as a planar coil array, in particular as an axially symmetrical planar coil array or in particular with a saddle coil as a primary coil. In further typical embodiments, the coil is realized as an annular coil or as a saddle coil.

Typically, the coil, in the axial direction, has a coil length corresponding to at least 0.8 times, in particular at least 1 time the outer diameter of the intramedullary nail or at most 2.5 times the outer diameter of the intramedullary nail. A winding number of the coil may be adapted, for example, depending on the outer diameter of the mandrel or the coil length.

In typical embodiments, a coil envelope, in particular a coaxial coil envelope, surrounds the coil, wherein the coil envelope at least substantially is composed of a non-metallic material. Typically, the coil envelope is produced of at least 70%, in particular at least 80% or at least 90% of a non-metallic material. Typically, the non-metallic material comprises plastics, for example, epoxy resin, silicone or thermoplastic resin, or ceramics or glass. Typically, a plastic material used for producing the coil envelope is biocompatible. Typically, the coil envelope is produced by overmolding or overcasting the coil with plastic material. A production by overcasting may be advantageous, for example, since mechanical forces for fixing a coil to be overcast or one or more tube piece/s to be overcast do not occur.

In typical embodiments, the coil envelope is produced by overcasting or overmolding a coil arranged at the first tube with plastic material. In exemplary embodiments, the coil envelope is produced by overmolding the coil in an injection mold. In further typical embodiments, the coil envelope is produced by overmolding a coil arranged at a tube piece of a first tube of multi-piece realization with plastic material, wherein the overmolding is performed before the tube pieces of the first tube are joined.

Typically, the coil envelope is at least substantially permeable for alternating electromagnetic fields, in particular for alternating fields having frequencies of at least 1 kHz, for example of at least 10 kHz or of at least 100 kHz, or of a maximum of 1 GHz, for example of a maximum of 100 MHz or of a maximum of 10 MHz.

In typical embodiments, the coil envelope fills the coil area at least substantially radially to the outside in a flush manner with an outer contour of the first tube. In typical embodiments, the coil envelope is oriented to be coaxial to the coil or coaxial to the longitudinal axis of the intramedullary nail. Typically, the coil envelope surrounds the coil or the first tube, in particular in the coil area, substantially in a ring-shaped manner.

In typical embodiments, the first tube comprises a coil core arranged radially inside the coil. Typically, the coil core is a ferrite core. Typically, the coil core is realized to be hollow. Typically, the coil is arranged at the coil core. Typically, the coil core and the coil are encapsulated by means of plastic material, for example, using epoxy resin. Typically, the coil core is arranged coaxially with the intramedullary nail.

In typical embodiments, the coil core has an axial projection at an axial end of the coil. Typically, the coil core has a radial projection at both axial ends. Typically, the radial projection is adapted to shield the windings of the core from metallic tube pieces. Typically, the radial projection forms a radial stop for the windings of the coil.

Typically, the first tube is realized in the coil area or in the portion having the smaller outer diameter to be at least substantially full. In particular, the cross-sectional area of the first tube in the coil area is full by at least 30%, for example by at least 50%, at least 70% or is full by at least 90%. In typical embodiments, the first tube in the coil area is formed by a mandrel realized as a full cylinder.

In typical embodiments, the first tube has a second locking opening in an intermediate area between the coil area and the second tube. Typically, the second locking opening is realized in an intermediate part of the first tube, wherein the intermediate piece is arranged axially at the side of the coil area facing the second tube, in particular in the intermediate area between a mandrel and a hollow piece of the first tube.

In typical embodiments, the distance between the first locking opening and the second locking opening amounts to a maximum of 30 mm, in particular to a maximum of 25 mm.

Typically, the intramedullary nail comprises a drive which is electrically connected to the coil. Typically, the drive is arranged in the first tube between the coil area and the second tube, in particular between an intermediate piece and the second tube. Typically, an electrical connection between the coil and the drive is realized by a feedthrough, in particular through an intermediate piece. The feedthrough is realized in the axial direction, for example. Typically, the feedthrough is drilled. In typical embodiments, the drive comprises a motor, in particular an electric motor. Typically, the drive comprises a gear, for example, a multi-stage planetary gear. In typical embodiments, the drive comprises an electronics system or a sensor system for controlling and monitoring the drive. Typically, the drive comprises an electrical energy storage.

In typical embodiments, the outer diameter of the first tube in the coil area, in particular the outer diameter of the mandrel in the coil area, is larger than the diameter of the first locking opening or than the diameter of the second locking opening. Typically, the outer diameter of the mandrel of the first tube in the coil area is larger than the diameter of the first locking opening or than the diameter of the second locking opening. Typically, the first tube in the coil area has an outer diameter of the mandrel of at least 2 mm, in particular of at least 4 mm or of at least 6 mm. The first tube in the coil area has an outer diameter of the mandrel which is at least by 1 mm, in particular at least by 1.5 mm or at least by 2 mm smaller than the outer diameter of the coil envelope.

In typical embodiments, the mandrel of the first tube has a radial fillet axially toward an intermediate piece of the first tube. The radial fillet may be advantageous to transfer mechanical bending loads between the mandrel and the intermediate piece. Typically, a coil core arranged at the mandrel, has a recess matched to the radial fillet. Typically, the mandrel and the intermediate piece are produced in one piece.

In typical embodiments, an intermediate piece of the first tube has axial protrusions axially in the direction of the second tube, which are adapted for interlocking the intermediate piece with a hollow piece of the first tube. In further typical embodiments, the intermediate piece and the hollow piece are welded together.

In typical embodiments, the first tube has a third locking opening between the first locking opening and the coil area or in an intermediate area between the coil area and a hollow piece of the first tube.

Typically, the second tube has a further locking opening, in particular at the end of the second tube opposite the first tube.

In typical embodiments for transferring energy from a primary coil to a coil of the intramedullary nail, the primary coil is in particular arranged around the coil of the intramedullary nail or in the proximity of the coil of the intramedullary nail, in particular on the skin of a patient or a treated animal Typically, when the primary coil is energized, an electric voltage, in particular an alternating voltage is applied to the primary coil, and a first current, in particular an alternating current, flows through the primary coil. The energized primary coil typically generates an alternating magnetic field. Typically, the reception of the energy is performed by the coil of the intramedullary nail, in that a second current is induced in the coil of the intramedullary nail by the alternating magnetic field. The energy transferred from the primary coil to the coil of the intramedullary nail, in particular in the form of pulses generated by the primary coil, may be utilized, for example, to drive a gear of the intramedullary nail, in particular to drive a gear of the intramedullary nail in real time so as to power an electronics system of the intramedullary nail or to charge an electrical energy storage of the intramedullary nail.

Typical advantages of embodiments comprise, for example, that the intramedullary nails require less space. Typical intramedullary nails may also be implanted in case of a low osteotomy height or close to a joint. Further advantages may be that the intramedullary nails permit high energy transmission performance or have high energy transmission efficiency. Typical intramedullary nails may permit a more targeted control, may have increased reliability, or may provide a higher distracting force. A further advantage may be that no feed line from a coil arranged outside the intramedullary nail to the intramedullary nail is necessary. Intramedullary nails of typical embodiments may enable shorter and simplified surgery for implanting or removing an intramedullary nail.

BRIEF DESCRIPTION OF THE DRAWINGS

Hereinafter, exemplary embodiments of the invention are explained in more detail on the basis of drawings. Shown are in:

FIG. 5A a schematic sectional view of a detail of an intramedullary nail, wherein a first locking opening and a second locking opening are twisted relative to one another;

FIG. 5B a schematic sectional view of a detail of an intramedullary nail, wherein a first locking opening and a second locking opening are oriented obliquely to the longitudinal axis of the intramedullary nail;

FIG. 6 a schematic sectional view of a detail of an intramedullary nail with a multi-part end piece; and FIG. 7 a schematic sectional view of a detail of an intramedullary nail, wherein a mandrel of the first tube has a radial fillet toward an intermediate piece.

Figure 1:
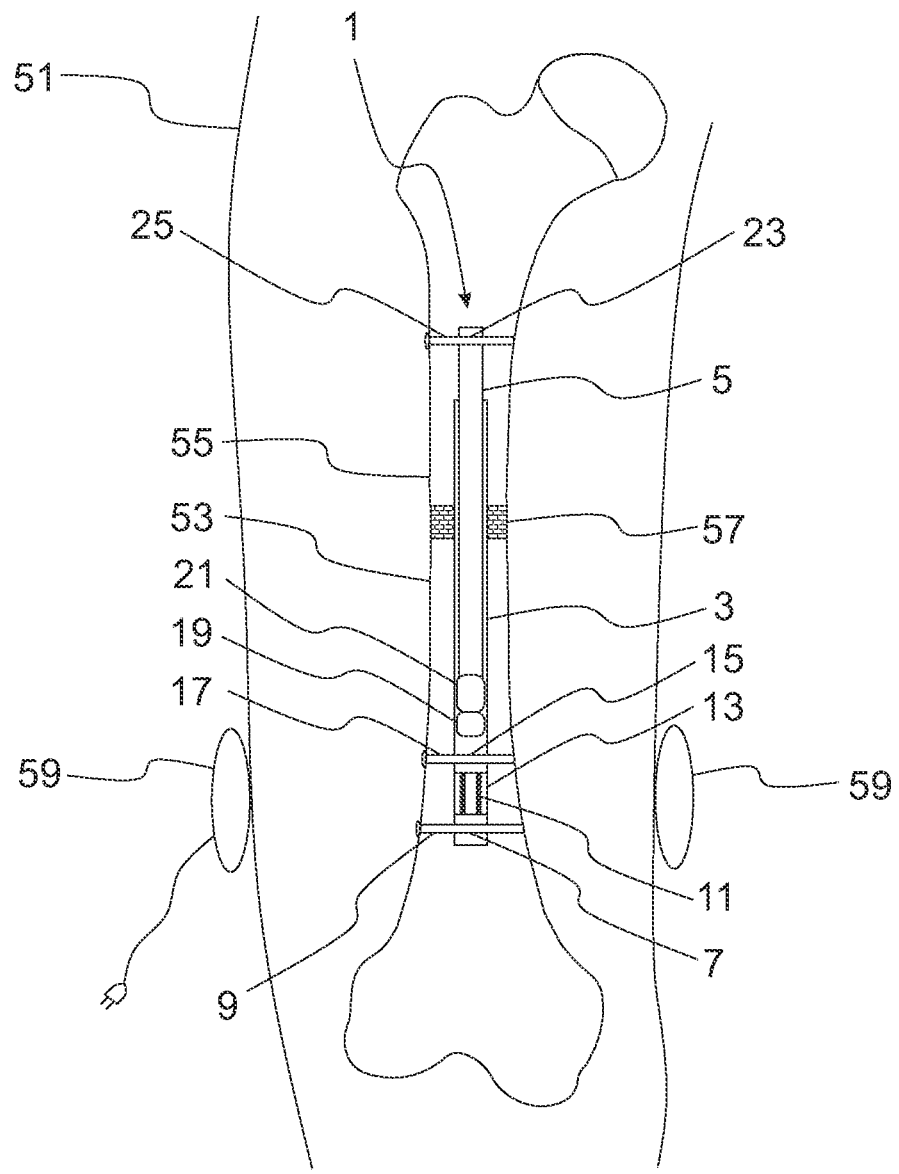
FIG. 1 a schematic overview sketch of an intramedullary nail for distracting a long bone, in a sectional view.

DESCRIPTION OF THE EXEMPLARY
EMBODIMENTS SHOWN IN THE FIGURES

Hereinafter, typical embodiments of the invention will be described, wherein identical reference numerals will be used in parts for identical or similar parts and will may possibly not be explained again with each Figure. The invention is not restricted to the typical embodiments described below. For reasons of better clarity, not all of the respective features are in parts provided with a reference numeral, in particular when features are assigned to an element encompassing the longitudinal axis of the intramedullary nail once or several times, for example, the coil core with the reference numeral 27 of FIG. 2.

FIG. 1 shows a schematic overview sketch of an intramedullary nail 1 for distracting a long bone of a patient 51. The intramedullary nail 1 is arranged within the long bone, wherein a first tube 3 of the intramedullary nail 1 is locked with a first bone fragment 53, and a second tube 5 is locked with a second bone fragment 55. The second tube 5 is connected to the first tube 3 to be axially displaceable within one another. In FIG. 1, the second tube 5 is partially introduced into the first tube 3 and displaceable in the axial direction relative to the first tube 3.

In FIG. 1, the first tube 3 has a first locking opening 7 in an end area at the end of the first tube 3 opposite the second tube 5. A first locking means 9, in FIG. 1 a bolt, is introduced into the first bone fragment 43 and positioned through the first locking opening 7.

Between the first locking opening 7 and the second tube 5, a coil 11 is arranged at the first tube 3 in a coil area. In the coil area, the first tube 3 has a smaller diameter, in particular as compared to the outer diameter of the first tube 3 in the adjacent end area or in an intermediate area, which is axially adjacent to the coil area in the direction of the second tube 5. In the coil area, the coil 11 is surrounded by a coil envelope 13. In FIG. 1, the coil envelope 13 fills out the coil area radially to the outside to be flush with the outer diameter of the first tube 3 in the end area and flush with the outer diameter of the first tube 3 in the intermediate area.

In FIG. 1, the coil 11 is realized as a cylindrical coil. A primary coil 59, realized, for example, as an annular coil in FIG. 1, is arranged extracorporeally on the patient 51, in particular around the coil 11. The primary coil 59 is adapted to provide an alternating magnetic field in order to transfer energy inductively to the intramedullary nail 1, in particular to the coil 11, by the alternating magnetic field inducing current in the coil 11.

In the intermediate area between the coil area and the second tube 5, a second locking opening 15 is arranged. A second locking means 17 is introduced into the first bone fragment 53 and positioned through the second locking opening 15.

A drive is arranged between the second tube 5 and the coil 11, in FIG. 1, for example, between the second tube 5 and the second locking opening 15. Typically, the drive, in FIG. 1 a motor 19, in particular an electric motor, and a gear 21 are adapted to move the first tube 3 and the second tube 5 axially toward one another. For distracting the long bone, the second tube 5 is moved slowly out of the first tube 3 in FIG. 1, so that the first bone fragment 53 and the second bone fragment 55 are moved apart and the long bone is extended. In the ossification zone 57, new bone tissue may grow in this case. In FIG. 1, the drive is supplied with energy via the coil 11.

In the second tube, a further locking opening 23 is arranged at the end of the second tube 5 opposite the first tube 3. A further locking means 25 is introduced into the second bone fragment 55 and positioned through the further locking opening 23. The further locking means 25 locks the second bone fragment 55 via the further locking opening 23 with the second tube 5. For reasons of better clarity, the locking means were not plotted in the further Figures.

Figure 2:
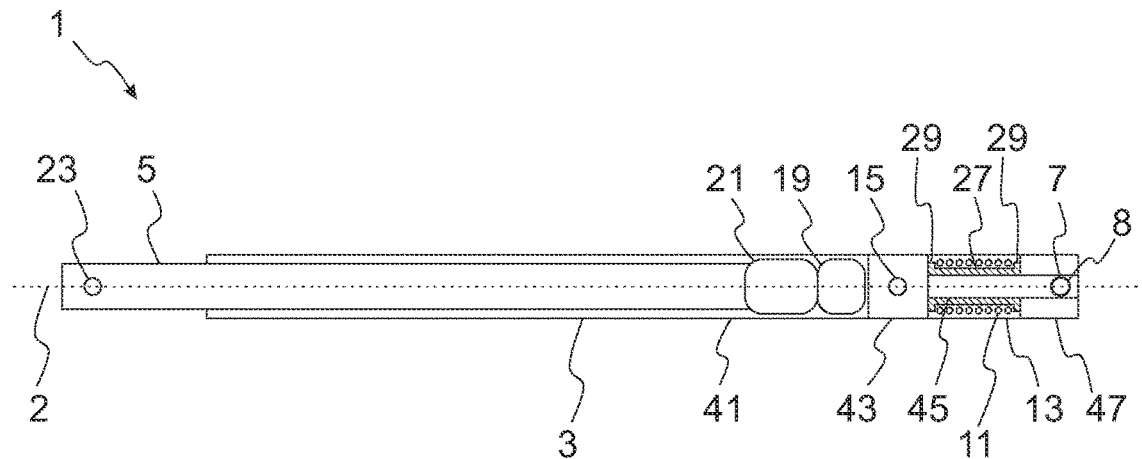
FIG. 2 a schematic sectional view of an intramedullary nail.

FIG. 2 shows a schematic side view of an intramedullary nail 1 with a first tube 3 and a second tube 5, which are arranged along the longitudinal axis 2 of the intramedullary nail 1. The second tube 5 is partially arranged within the first tube 3 and axially displaceable relative to the first tube 3. The second tube 5, a motor 19, and a gear 21 are arranged in a hollow piece 41 of the first tube 3. In an end area at the end of the first tube 3 opposite the second tube 5, an end piece 47 of the first tube 3 is arranged. The end piece 47 encloses a mandrel 45 of the first tube 3, which protrudes into the end area from a coil area of the first tube 3 adjacent to the end area. A first locking opening 7 extends through a metal sleeve 8. The metal sleeve 8 is inserted through a mandrel opening of the mandrel 45 and an end piece opening of the end piece 47. The mandrel opening of the mandrel 45 and the end piece opening of the end piece 47 are arranged to be aligned with one another. The metal sleeve 8 is welded to the end piece 47 along the circumference of the end piece opening.

In further exemplary embodiments, the mandrel is directly welded, bonded to the end piece or otherwise connected to it.

In the coil area, the first tube 3 comprises the mandrel 45 and a coil core 27 arranged radially outside around the mandrel 45. The mandrel 45 has a smaller outer diameter than the end piece 47 or than an intermediate piece 43 adjacent to the mandrel 45, which intermediate piece is arranged between the coil area and the hollow piece 41. In FIG. 2, the mandrel 45 and the intermediate piece 43 are produced of metal. The mandrel 45 is produced in one piece with the intermediate piece 43.

In FIG. 2, the coil core 27 is realized as a ferrite core. Axially in the direction of the end piece 47 and the intermediate piece 43, the coil core 25 respectively has a radial projection 29. A coil 11 is arranged radially outside on the coil core 27 and encompasses the coil core 27. In FIG. 2, the coil 11 is realized as a cylindrical coil. The coil 11 is arranged between the radial projections 29 of the coil core 27.

The radial projections 29 of the coil core 27 are in particular advantageous in the event that adjacent tube pieces such as the intermediate piece 43 or the end piece 47 are made of metal. The coil core 27 can shield the coil 11, in particular windings of the coil 11, or a magnetic flux through the coil core 27 from the adjacent tube pieces.

The coil core 27 and the coil 11 are surrounded by a coil envelope 13 radially toward the outside. The coil envelope 13 is produced by casting the coil area of the first tube 3 with plastic material.

In FIG. 2, the intermediate piece 43 has a second locking opening 15. The intermediate piece 43 comprises axial protrusions toward the second tube 5, which interlock with the hollow piece 41. The hollow piece 41 is radially welded together with the intermediate piece 43. The intermediate piece 43 has an axial bore, through which an electrical connection between the coil 11 and the motor 19 is guided. In further exemplary embodiments, the bore is realized to be partially or completely wound.

Figure 3:
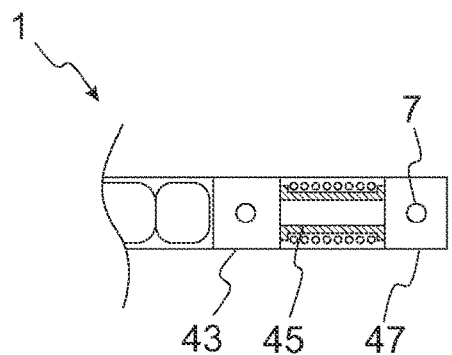
FIG. 3 a schematic sectional view of a detail of a further embodiment of an intramedullary nail.

FIG. 3 shows a detail of a further embodiment of an intramedullary nail 1. In FIG. 3, a mandrel 45 of a first tube 3 is welded together with an end piece 47 of the first tube 3 and does at least not substantially protrude into the end piece 47. Typically, the mandrel 45 is welded together with the end piece 47 at the front side. A first locking opening 7 does not extend through the mandrel 45. The intermediate piece 43 is realized in one piece with the mandrel 45.

Figure 4A:
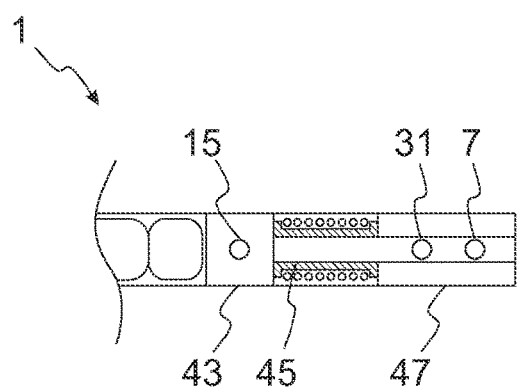
FIG. 4A a schematic sectional view of a detail of an intramedullary nail with a third locking opening.

In FIG. 4A, a first tube of the intramedullary nail 1, apart from a first locking opening 7 in the end area of the first tube 3 and a second locking opening 15 in an intermediate piece 43 of the first tube, has a third locking opening 31 between the first locking opening 7 and the coil area.

Figure 4B:
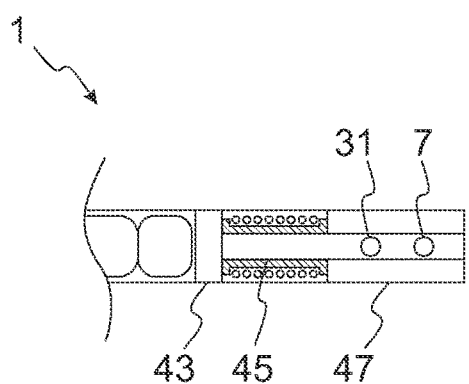
FIG. 4B a schematic sectional view of a detail of an intramedullary nail without any locking opening in an intermediate piece of a first tube.

FIG. 4B shows an embodiment similar to FIG. 4A, however, without a second locking opening 15 in the intermediate piece 43. In FIG. 4A and FIG. 4B, the first locking opening 7 and the third locking opening 31 extend through the end piece 47 and the mandrel 45. In further embodiments, the mandrel 45, similar to FIG. 3, may protrude into the end piece 47 by a shorter way or not at all, and the first locking opening 7 or the third locking opening 31 may not be realized by the mandrel 45.

FIG. 5A and FIG. 5B show intramedullary nails 1 with locking openings twisted relative to one another or locking openings oriented obliquely to the longitudinal axis 2 of the intramedullary nail 1. In FIG. 5A, the first locking opening 7 and the second locking opening 15 are oriented in different radial directions. In FIG. 5B, the first locking opening 7 and the second locking opening 15 are oriented obliquely to the longitudinal axis 2 of the intramedullary nail 1. In FIG. 5B, the first locking opening 7 and the second locking opening 15 are oriented toward a common point of intersection.

FIG. 6 shows a further embodiment of an intramedullary nail 1 with a multi-part end piece 47. The end piece 47 comprises a first end piece 33, a second end piece 35, and a thread insert 37. In FIG. 6, the first end piece 33 is realized as a metal sleeve. The first end piece 33 is inserted through a mandrel opening 46 of a mandrel 45. The first locking opening 7 extends through the end piece 33. In FIG. 6, the first locking opening 7 and the second locking opening 15 are oriented in the viewing plane of FIG. 6. The mandrel 45 encompasses the first end piece 33 and protrudes into the second end piece 35. The intermediate piece 43 is produced in one piece with the mandrel 45. The coil envelope 13 and the second end piece 35 are produced by overmolding the intermediate piece 43, in particular along an axial portion of the intermediate piece 43, the mandrel 45, the coil core 27, the coil 11, the first end piece 33, and the thread insert 37 with biocompatible plastic material in an injection mold.

In further exemplary embodiments, there is no thread insert. In such exemplary embodiments, a thread insert is introduced subsequently into the plastic material, in particular screwed in.

In FIG. 6, the intermediate piece 43 of the first piece has a radial recess 44 toward the coil area. The coil envelope 13 extends axially into the radial recess 44. In the radial recess, the first tube and the coil envelope 13 are connected in a form-fit manner.

FIG. 7 shows a schematic sectional view of an intermedullary nail 1 with a mandrel 45, which has a radial fillet 39 toward an intermediate piece 43. The radial fillet 39 may be advantageous to improve the transmission of bending loads between the mandrel 45 and the intermediate piece 43, in particular between a first locking opening (not illustrated) and the second locking opening 15. In the direction of the intermediate piece 43, the coil core 27 axially has a recess matched to the fillet 39. The radial fillet 39, in particular with the matched recess in the coil core 27, is not restricted to the exemplary embodiment of FIG. 7 but may also be realized in the exemplary embodiments of FIGS. 1 to 6.

The invention is not restricted to the exemplary embodiments described above, the scope of the invention is rather determined by the claims. In particular, not all of the illustrated parts necessarily are features of the invention, this applies particularly to the illustrated human bone.

The invention claimed is:

1. An intramedullary nail for distracting a long bone, comprising
a first tube extending in an axial direction of the intramedullary nail,
a second tube extending in the axial direction of the intramedullary nail, which second tube is coupled with the first tube to be axially displaceable within one another,
a first locking opening, for locking the intramedullary nail in a bone fragment of the long bone, in an end area of the first tube facing away from the second tube,
a coil, which is disposed in a coil area of the first tube between the first locking opening and the second tube, and
a drive which is electrically connected to the coil,
wherein the first tube extends uninterrupted in the axial direction between the first locking opening and the second tube, wherein the first tube has an outer constricted section in the coil area, and wherein the coil is wound around said outer constricted section of the first tube, wherein in the coil area the coil is arranged radially outside the first tube.

2. The intramedullary nail according to claim 1, wherein a coil envelope surrounds the coil, and wherein the coil envelope at least substantially is composed of a non-metallic material.

3. The intramedullary nail according to claim 2 wherein the coil envelope is produced by overcasting or overmolding the coil arranged on the first tube with plastic material.

4. The intramedullary nail according to claim 2, wherein the coil envelope fills the coil area at least substantially radially outward in a flush manner with an outer contour of the first tube.

5. The intramedullary nail according to claim 2, wherein the coil is a cylindrical coil and is arranged coaxially with the intramedullary nail.

6. The intramedullary nail according to claim 1, wherein the first tube comprises a coil core arranged radially inside the coil.

7. The intramedullary nail according to claim 6, wherein the coil core has a radial projection at an axial end of the coil.

8. The intramedullary nail according to claim 1, wherein the first tube is produced of at least two interconnected tube pieces.

9. The intramedullary nail according to claim 1, wherein the first tube is realized in the coil area to be at least substantially full.

10. The intramedullary nail according to claim 1, wherein the first tube has a second locking opening in an intermediate area between the coil area and the second tube.

11. The intramedullary nail according to claim 10, wherein a distance between the first locking opening and the second locking opening amounts to a maximum of 30 mm.

12. The intramedullary nail according to claim 10, wherein a distance between the first locking opening and the second locking opening amounts to a maximum of 25 mm.

13. The intramedullary nail according to claim 1, wherein an outer diameter of the first tube in the coil area is larger than the diameter of the first locking opening or than the diameter of a second locking opening.

14. A method for transmitting electromagnetic energy from a primary coil to a coil of an intramedullary nail according to claim 1, including
energizing the primary coil, and
receiving, by the coil of the intramedullary nail, at least a part of the electromagnetic energy emitted by energizing the primary coil.

* * * * *